United States Patent
Della Valle et al.

(10) Patent No.: US 9,402,818 B2
(45) Date of Patent: Aug. 2, 2016

(54) USE OF AMIDES OF MONO- AND DICARBOXYLIC ACIDS IN THE TREATMENT OF RENAL DISEASES

(71) Applicant: Epitech Group S.r.l., Milan (IT)

(72) Inventors: Francesco Della Valle, Milan (IT); Raffaele Migliaccio, Monza (IT); Maria Federica Della Valle, Padova (IT)

(73) Assignee: Epitech Group S.r.l., Milan (IT)

( * ) Notice: Subject to any disclaimer, the term of this patent is extended or adjusted under 35 U.S.C. 154(b) by 0 days.

(21) Appl. No.: 14/536,186

(22) Filed: Nov. 7, 2014

(65) Prior Publication Data

US 2015/0065576 A1 Mar. 5, 2015

Related U.S. Application Data

(62) Division of application No. 13/251,871, filed on Oct. 3, 2011, now abandoned.

(30) Foreign Application Priority Data

Oct. 4, 2010 (EP) .................................... 10425319

(51) Int. Cl.
*A61K 31/164* (2006.01)
*A61K 31/198* (2006.01)

(52) U.S. Cl.
CPC ............. *A61K 31/164* (2013.01); *A61K 31/198* (2013.01)

(58) Field of Classification Search
CPC ............................ A61K 31/164; A61K 31/198
USPC ................................................ 514/616, 625
See application file for complete search history.

(56) References Cited

U.S. PATENT DOCUMENTS

| 5,618,842 | A | 4/1997 | Della Valle et al. |
| 6,548,550 | B1 | 4/2003 | Comelli et al. |
| 2003/0215513 | A1 | 11/2003 | Fyhr et al. |

FOREIGN PATENT DOCUMENTS

| EP | 1 844 784 A1 | 10/2007 |
| WO | WO 2005/115370 A2 | 12/2005 |
| WO | WO 2007/124169 A2 | 11/2007 |
| WO | WO 2008/023998 A1 | 2/2008 |
| WO | WO 2008/075978 A2 | 6/2008 |
| WO | WO 2008075978 A2 * | 6/2008 |
| WO | WO 2010/129845 A1 | 11/2010 |

OTHER PUBLICATIONS

Lars Järup, Occupational and Environmental Medicine, 1995; 52:818-822.
Lo Verme et al. Molecular Pharmacology, Jan. 2005, vol. 65 No. 1 pp. 15-29.
Kume et al, "Peroxisome Proliferator-Activated Receptors in Diabetic Nephropathy", PPAR Research, vol. 2008, pp. 1-11.
Park et al., Diabetes, Apr. 2006, vol. 55, No. 4, pp. 885-893.

\* cited by examiner

*Primary Examiner* — Jennifer M Kim
(74) *Attorney, Agent, or Firm* — Blank Rome LLP

(57) ABSTRACT

A therapy for renal diseases, in particular renal diseases, which develop in diabetic patients or patients who have been subjected to a treatment with an antitumor chemotherapy such as a platinum derivative and more generally cytotoxic drugs at renal level for treating of neoplastic diseases. More particularly, palmitoylethanolamide and diethanolamide of fumaric acid are used in the treatment of renal diseases, in particular those caused by dysmetabolic diseases or by toxic or chemotherapy agents, such as platinum derivatives. Palmitoylethanolamide is used preferably in micronized or ultramicronized form. Diethanolamide of fumaric acid is used preferably in aqueous solution.

3 Claims, No Drawings

USE OF AMIDES OF MONO- AND DICARBOXYLIC ACIDS IN THE TREATMENT OF RENAL DISEASES

This is a divisional of U.S. application Ser. No. 13/251,871, filed Oct. 3, 2011, now abandoned.

FIELD OF THE INVENTION

The present invention regards a therapy for renal diseases and the ensuing alterations of the renal function, in particular, even though not exclusively, of the renal diseases which develop in diabetic patients or who have been subjected to a chemotherapy antitumor treatment using a platinum derivative.

BACKGROUND OF THE INVENTION

The chronic renal disease and renal failure which derives therefrom are extremely frequent diseases even though under-diagnosed; actually, it is estimated that 17% of the adult population is affected by this disease.

The most frequent renal disease is characterised by damaged renal glomeruli.

Renal diseases may be congenital or acquired; in particular the acquired ones may have various etiology:

immunologic like the Goodpasture's syndrome, lupus nephritis and immunoglobulin A nephropathy. In the case of the immunologically mediated renal disease, the cause lies in the presence of a strong antigenic stimulus which triggers an immune reaction;

dysmetabolic and in particular diabetic nephropathy, one of the most common causes of chronic renal disease. The prevalence is of 20-30% in patients suffering from type 1 diabetes and about 10% of the cases in patients suffering from type 2 diabetes. This is an insidious disease in that it is characterised by a particularly slow occurrence (up to 20-30 years from the occurrence of diabetes) and it is practically asymptomatic over a long period of time; it initially occurs through a microalbuminuria (an amount of albumin in the urine comprised between 30 and 300 mg/l) which slowly develops into macroalbuminuria indicating a manifest nephropathy (an amount of albumin in the urine exceeding 300 mg/l, up to reaching values of 3 g within 24 hours);

hemodynamic, due to arterial hypertension. An alteration in the pressure mechanisms of the renal blood flow leads, over time, to a reduction of the renal filtering capacity;

ischemic. Renal ischemia is the most frequent pathogenic event involved in acute renal disease and in the ensuing tubular necrosis, both in native and transplanted kidneys;

toxic. Most of the clinically important drugs (cytotoxic agents, chemotherapy agents, nonsteroidal anti-inflammatory drugs, corticosteroid therapies, etc) and various chemical products (such as radiologic contrast media, solvents, etc) produce nephrotoxicities capable of very frequently causing inflammation at the renal parenchymal level and functional insufficiency both transitory and chronic.

Even in veterinary medicine, renal diseases bound to develop into chronic renal disease constitute an important clinical category, representing the second cause of death in dogs, after diseases of tumour origin, and the first cause of death of the aged cats. From an etiologic point of view, the causes that determine the loss, progressive and irreversible, of the functionality of the nephrons in small animals were precisely classified in (Squires et al, 1998) in:

Degenerative: chronic interstitial nephritis; renal infarction
Autoimmune: Anti-GBM glomerulonephritis
Metabolic: diabetes; hyperthyroidism (cats); hypercalcemia
Neoplastic: renal lymphomas and carcinomas
Idiopathic: amyloidosis; idiopathic glomerulonephritis
Infective: bacterial pyelonephritis; Lyme nephropathy (Borreliosis)
Immune-mediated: immune-complex glomerulonephritis
Toxic: nephrotoxic drugs (e.g. cisplatin, aminoglycosides, NSAIDs)
Traumatic: rupture of bladder and urethra.

In any case, regardless of the etiology, in all acquired renal diseases, both in humans and animals, there is an activation of the inflammatory processes primarily aimed at countering the harmful events but which may become the cause of renal glomerulosclerosis and of tubulointerstitial fibrosis capable of determining the development of chronic renal disease up to the pre-End stage (pre-End Stage Renal Disease) wherein most of the nephrons are destroyed. One of the two main objectives of nephrology is, first and foremost, that of understanding the mechanism which regulates the passage from an acute renal damage to the chronic fibrotic renal disease given that, once the fibrogenesis has started it might be very difficult, currently, to intervene on the fibrotic process; in any case, the objective of stopping or at least slowing the progression of the chronic renal disease remains extremely important considering that such disease also constitutes an important risk factor for cardiovascular diseases. Regarding this, currently there are several studies aimed at accurately understanding the most significant mechanisms of occurrence, with the aim of preventing the phenomena that determines the irreversibility of the disease. Among these phenomena, the most significant one is that which induces tubulointerstitial fibrosis considered the main cause of the chronic renal disease; fibrosis causes an excessive accumulation of extracellular type, mainly made up collagen, and it is usually accompanied by a progressive loss of renal function when the normal tissue is replaced by a cicatricial tissue. One of the most currently studied phenomena is constituted by processes of controlling the genesis of mio-fibroblasts and by the role played by these cells in the formation of the fibrotic cicatricial tissue. In particular such studies try to understand the reason why a reparative phenomenon usually provided for by the tissue, like the renal one, continuously subjected to an extensive amount of noxae, may at one point determine an excessive increase of the extracellular matrix and thus a tubulointerstitial fibrosis. Particular attention is currently paid to the genesis of mio-fibroblasts both starting from tubular-epithelial cells and from endothelial cells through a process of phenotypic transformation from epithelial to mesenchymal, potently stimulated by the TGF-1β (Transforming Growth Factor). Actually, the TGF-1β expression constantly increases in the renal tubular epithelium during an active process of fibrogenesis. In animal models of renal damage, the dose in the renal tubular epithelium of the TGF-1β is considered an interesting indication of the state of activation of fibrogenesis and, hence the state of functional alteration induced by the renal disease.

Regardless of the extensive new information regarding the pathogenic mechanisms involved in the development of renal diseases, satisfactory therapeutic solutions for controlling these conditions are yet to be discovered.

Palmitoylethanolamide (PEA) is the parent of a family of N-acyl amides called Aliamides: a class of endogenous lipid molecules capable of normalizing the activity of immune cells through a local antagonist mechanism. The analgesic effects, instead, are related to a normalisation of the controlled release of trophic factors like NGF which, if present in excess in the tissues, make the neuronal structures hypersensitive and hyperexcitable, with the occurrence of hyperalgesia and allodynia. From a clinical point of view, the oral uptake of products containing PEA is capable of improving the neuropathic symptomatology related to the peripheral neuropathy also promoting the functional recovery of the motor conduction velocity. PEA, at experimental level, is also efficient in dysmetabolic neuropathies, in particular administration thereof to animals made diabetic with streptozotocin eliminates allodynia and induces a partial recovery of the body weight and an increase of the insulin blood levels. These animals also reveal low over-production of blood free radicals and the levels of NGF in the sciatic nerve.

Analogously to the PEA, given N-acyl amides, generally formed from monoethanolamine and dicarboxylic fatty acids, saturated and unsaturated, per se non-physiologic but equally capable of forming, during catabolism, substances physiologically present in the organism of mammals, thus not determining accumulation and/or toxicity of any kind, proved capable of determining pharmacological effects similar to the parent PEA.

SUMMARY OF THE INVENTION

Now, we have surprisingly discovered that some molecules belonging to the class of the amides between an amino alcohol and a mono- or dicarboxylic acid are active in the treatment of renal diseases. In particular, it was observed that palmitoylethanolamide (PEA) and diethanolamide of fumaric acid, a monounsaturate dicarboxylic fatty acid normally present in the organism of mammals, revealed a considerable activity with respect to said diseases.

Thus, a first object of the present invention is constituted by a mono- or diamide of a C12-C20 monocarboxylic acid, saturated or monounsaturated, or of a C4-C14 dicarboxylic acid, saturated or monounsaturated, respectively, with an amine selected from among monoethanolamine and serine, or mixtures thereof, for use in the treatment of renal diseases, in particular but not exclusively renal diseases caused by dysmetabolic diseases or by toxic agents.

A further object of the present invention is represented by palmitoylethanolamide (PEA) for use in the treatment of renal diseases, wherein PEA is preferably in micronized form or in ultra-micronized form.

A further object of the present invention is constituted by PEA for use in the treatment of renal diseases, wherein said PEA is administered orally.

A further object of the present invention is constituted by diethanolamide of fumaric acid for use in the treatment of renal diseases, in aqueous solution.

DETAILED DESCRIPTION OF THE INVENTION

The present invention is based on the surprising discovery that the exogenous administration of a mono- or diamide of a C12-C20 monocarboxylic acid, saturated or monounsaturated, or of a C4-C14 dicarboxylic acid, saturated or monounsaturated, respectively, with an amine selected from among monoethanolamine and serine and in particular oral administration of Palmitoylethanolamide preferably in micronized form (PEAm) or in ultra-micronized form (PEAum) and/or of diethanolamide of fumaric acid, administered preferably in solubilised form in suitable aqueous media, is capable of substantially improving the renal function in a mammal affected by the renal disease, with particular reference to diabetic nephropathy and nephropathy from anti-tumor agents. The present inventors also discovered that the improvement of the renal function is associated to a lower expression of the TGF-1β considered a considerable indication of the fibrogenesis in progress. The improvement of the renal function is also confirmed in patients affected by inflammatory nephropathy and diabetic nephropathy.

In an embodiment of the invention, said C12-C20 monocarboxylic acid, saturated or monounsaturated, is selected from among palmitic acid, stearic acid and oleic acid.

In an embodiment of the invention, said C4-C14 dicarboxylic acid, saturated or monounsaturated, is selected from among fumaric acid, azelaic acid and trans-traumatic acid.

Palmitoylethanolamide is a commercial product, which can be prepared through conventional methods, well known to a man skilled in the art, such as those that provide for the reaction between ethanolamine or serine, possibly in protected form, and said mono- or dicarboxylic acid in suitable conditions of condensation, which may also provide for the use of condensing agents.

The term "PEA in micronized form" or "PEAm" is used to indicate palmitoylethanolamide in which at least 94% or at least 95% or about 96% of the particles has a dimension smaller than 10 microns and preferably at least 77% or at least 78% or about 80% of the particles has a dimension smaller than 6 microns. PEAm may be prepared according to the disclosure of the European patent n° EP 1 207 870 B1.

The term "PEA in ultra-micronized form" or "PEAum" is used to indicate palmitoylethanolamide in which at least 97% or at least 98% or at least 99% or about 99.9% of the particles has dimensions smaller than 6 microns and preferably at least 57% or at least 58% or at least 59% or about 59.6% of the particles has dimensions smaller than 2 microns. PEAum may be prepared according to the disclosure of the Patent Application No. PCT/IT2009/000399.

Diethanolamide of fumaric acid may be prepared by synthesis according to the disclosure of Example 10 of U.S. Pat. No. 5,618,842.

Thus, the present invention regards a mono- or diamide of a C12-C20 monocarboxylic acid, saturated or monounsaturated, or of a C4-C14 dicarboxylic acid, saturated or monounsaturated, respectively, with an amine selected from among monoethanolamine and serine, or mixtures thereof, for use in the treatment of renal diseases, in particular but not exclusively renal diseases caused by dysmetabolic diseases or by toxic agents.

In an embodiment said mono- or diamide of a C12-C20 monocarboxylic acid, saturated or monounsaturated, or of a C4-C14 dicarboxylic acid, saturated or monounsaturated is PEA or diethanolamide of fumaric acid.

In an embodiment, PEA is used in micronized form (PEAm).

In a different embodiment, PEA is used in ultra-micronized form (PEAum), alone or mixed with PEAm.

In an embodiment, diethanolamide of fumaric acid is used in solubilised form in a suitable aqueous solvent.

Pharmacological Activity of the Compounds of the Invention

Occurrence of Renal Damage After Administration of Streptozootocin to Mice

The model of streptozootocin in mice represents a classic and known model of hyperglycemia capable of inducing a progressive renal damage into the animal leading to the renal disease with clear alterations of the characteristic parameters.

The model applied is as follows: male mice C57BL6/J were kept under standard conditions of care. Diabetes was induced into 8-weeks old mice and with an average weight of about 22 g by means of an intraperitoneal injection of streptozotocin in citrate buffer (55 mg/Kg of weight/day) for 5 consecutive days. The control animals were treated in the same conditions using the citrate buffer alone.

Treatments were administered orally, by means of a tube, using both micronized Palmitoylethanolamide- PEAm (10.0 mg/Kg) suspended in a carrier and ultra-micronized palmitoylethanolamide PEAum (10.0 mg/Kg) suspended in a carrier; the results were compared with control animals treated with the carrier alone. A 0.5% carboxymethyl cellulose was used as a carrier.

Diethanolamide of fumaric acid was administered in sterile aqueous saline solution by intraperitoneal injection (10.0 mg/Kg); the results were compared with the animals treated with sterile saline solution alone.

Administration of the carrier and of the two different suspensions containing palmitoylethanolamide or of the injection solution containing diethanolamide of fumaric acid, were performed once per day starting from the day of the last administration of Streptozotocin. Prior to sacrifice, the blood was collected from the saphenous vein using a micro syringe to determining, through conventional methods, the levels of glycemia, glycated haemoglobin and creatinine of the serum.

The evaluation of TGF-1β on the renal tissue was administered through the following method: small pieces of the renal cortex, carefully separated and weighed, were homogenised in Tris-HCl 10 mM buffer at 7.4 pH containing 2M of NaCl, 1 mM PMSF (phenylmethylsulfonyl fluoride, as a protease inhibitor), 1mM EDTA and 0.01% of Tween 80. The samples were centrifuged at 19,000 rpm for 30 minutes and the supernatant was collected, measured and preserved at −80° C. The evaluation of the TGF-1β was made using the ELISA commercial kit (Quantikine Kit™, Res & Diagn Systems, Minneapolis, USA) and the value expressed in pg/mg of total proteins. The concentration of total proteins was measured using the Bio-Rad commercial test (Hercules, Calif., USA).

The obtained results were gathered in Table 1.

TABLE 1

| Examined parameter | Non-diabetic animals (10 animals) | Diabetic animals treated orally with the carrier alone (10 animals) | Diabetic animals treated with micronized PEA-PEAm (10 animals) | Diabetic animals treated with ultra micronized PEA-PEAum (10 animals) | Diabetic animals treated by i.p. injection with saline solution alone (10 animals) | Diabetic animals treated by i.p. injection with diethanolamide of fumaric acid solubilised in saline solution (10 animals) |
|---|---|---|---|---|---|---|
| Body weight (g) | 27.82 ± 1.18 | 25.12 ± 1.10 | 26.52 ± 1.08 | 26.12 ± 1.21 | 24.43 ± 1.15 | 26.22 ± 1.02 |
| Glycemia (mg/dl) | 122.2 ± 5.62 | 408.45 ± 33.12 | 386.12 ± 36.76 | 380.34 ± 34.16 | 406.32 ± 33.44 | 386.19 ± 33.98 |
| Glycated haemoglobin % | 4.89 ± 0.05 | 12.80 ± 0.44 | 11.32 ± 0.38 | 11.01 ± 0.18 | 13.41 ± 0.63 | 12.12 ± 0.26 |
| Kidney weight/body weight | 6.65 ± 0.04 | 8.65 ± 0.85 | 7.85 ± 0.44 | 7.15 ± 0.38 | 9.00 ± 0.56 | 7.02 ± 0.46 |
| Amount of albumin excreted with urine (18 hrs prior to sacrifice) | 33.7 (26.2-41.5) | 340.5 (182.2-630.3) | 289.4 (166.4-480.6) | 151.5 (71.3-283.8) | 315.05 (201.3-582.4) | 135.7 (94.6-171.4) |
| Concentration of creatinine in the serum (mg/dl) | 0.21 ± 0.01 | 1.11 ± 0.02 | 0.81 ± 0.01 | 0.44 ± 0.01 | 1.51 ± 0.08 | 0.51 ± 0.03 |
| Level of TGF-1β (pg/mg) | 7.5 ± 0.8 | 24.2 ± 5.8 | 15.0 ± 3.0 | 10.3 ± 2.5 | 25.3 ± 4.6 | 11.7 ± 3.2 |

Occurrence of Renal Damage After Administration of Cisplatin to Mice

Cisplatin, a known and widely used chemotherapy agent, notoriously produces a serious renal damage in 50% of the patients subjected to treatment. Experimentally an animal model is used in mice, in which Cisplatin induces serious nephrotoxicity with ensuing renal disease. The model applied is as follows: male mice C57BL6/J were kept under standard conditions of care. Nephrotoxicity was induced into 8-weeks old mice and with an average weight of about 23 g, by means of an intraperitoneal injection of Cisplatin dihydrochloride in saline solution (20 mg/Kg in one administration). The control animals were treated in the same conditions using the saline solution alone. The animals were sacrificed 72 hrs after treatment with Cisplatin.

6 treatments were administered orally, one each 12 hrs by means of a tube, using both micronized palmitoylethanolamide-PEAm (10.0 mg/Kg) suspended in a carrier and ultra-micronized palmitoylethanolamide-PEAum (10.0 mg/Kg) suspended in a carrier; the first treatment was carried out 12 hours prior to the administration of the Cisplatin. The results were compared with control animals treated with the carrier alone. A 0.5% carboxymethyl cellulose solution was used as the carrier.

Diethanolamide of fumaric acid was administered in sterile aqueous saline solution by intraperitoneal injection (10.0 mg/Kg) with posology analogous to that of PEA; the results were compared with animals treated with sterile saline solution alone.

Prior to sacrifice, the blood was collected from the saphenous vein using a micro syringe to measure, through conventional methods, the levels of creatinine of the serum.

The level of TGF-1β on the renal tissue was measured through the following method:
small pieces of the renal cortex, carefully separated and weighed, were homogenised in Tris-HCl 10 mM buffer at a 7.4 pH containing 2M of NaCl, 1 mM PMSF (phenylmethylsulfonyl fluoride, as a protease inhibitor), 1 mM EDTA and 0.01% of Tween 80. The samples were centrifuged at 19,000 rpm for 30 minutes and the supernatant was collected, measured and preserved at −80° C. The amount of the TGF-1β was measured using the ELISA commercial kit (Quantikine Kit™, Res & Diagn Systems, Minneapolis, USA) and the value expressed in pg/mg of total proteins. The concentration of total proteins was measured using the Bio-Rad commercial test (Hercules, Calif., USA).

The obtained results were gathered in Table 2.

TABLE 2

| Examined parameter | Control animals (10 animals) | Animals with Cisplatin treated with the carrier alone (10 animals) | Animals with Cisplatin treated with micronized PEA-PEAm (10 animals) | Animals with Cisplatin treated with ultra micronized PEA-PEAum (10 animals) | Animals with cisplatin treated by i.p. injection with saline solution alone (10 animals) | Animals with cisplatin treated by i.p. injection with diethanolamide of fumaric acid solubilised in saline solution (10 animals) |
|---|---|---|---|---|---|---|
| Body weight (g) | 26.12 ± 1.11 | 23.10 ± 1.22 | 23.58 ± 1.13 | 24.55 ± 1.09 | 24.22 ± 1.45 | 24.15 ± 1.12 |
| Kidney weight/body weight | 6.44 ± 0.03 | 7.22 ± 0.80 | 7.85 ± 0.34 | 6.89 ± 0.42 | 8.15 ± 0.46 | 6.58 ± 0.26 |
| Amount of albumin excreted with urine (18 hrs prior to sacrifice) | 37.4 (31.7-44.6) | 363.75 (282.8-735.9) | 270.90 (206.9-405.8) | 175.9 (91.7-260.8) | 351.57 (258.1-623.4) | 181.4 (96.3-225.6) |
| Concentration of creatinine in the serum (mg/dl) | 0.22 ± 0.01 | 1.26 ± 0.05 | 0.92 ± 0.03 | 0.48 ± 0.02 | 1.36 ± 0.02 | 0.83 ± 0.06 |
| Dose of TGF-1β (pg/mg) | 8.2 ± 0.7 | 25.3 ± 6.0 | 15.8 ± 3.5 | 9.4 ± 3.2 | 22.1 ± 4.3 | 9.1 ± 2.8 |

Effect of Ultra-Micronized Palmitoylethanolamide-PEAum in nephropathic patients

Palmitoylethanolamide was administered to patients in form of tablets each containing 600 mg of active ingredient in ultra-micronized form; 2 tablets per day (one every 12 hours, after meals) were administered to patients for 60 consecutive days).

Determination of the GRF (Glomerular Filtration Rate) by the creatinine endogenous marker was carried out according to the US National Renal Foundation criteria (K/DOQI clinical practice guidelines for chronic kidney disease, 2002), using the Cockcroft-Gault equation (Cockcroft D. W. et al, 1976).

The results were indicated in Table 3.

TABLE 3

| | abbr | Age | Gender | Diagnosis | Glycemia under fasting | | GFR Glomerulal Filtration Rate (Creatinine Clearance) | |
|---|---|---|---|---|---|---|---|---|
| | | | | | T 0 | T 60 | T 0 | T 60 |
| Paz-01 | S.G. | 65 | F | Chronic Inflammatory nephropathy | N.D. | N.D. | 26.4 | 44.6 |
| Paz-02 | S.C. | 71 | M | Chronic Inflammatory nephropathy | N.D. | N.D. | 21.4 | 35.2 |
| Paz-03 | F.S. | 62 | F | Chronic Inflammatory nephropathy | N.D. | N.D. | 20.7 | 36.1 |
| Paz-04 | M.R. | 61 | M | Diabetic nephropathy (Diabetes type 2) | 210 mg/dl compensated with 10 U. ready insulin | 110 mg/dl compensated with 12 U. retard insulin | 18.9 | 41.4 |
| Paz-05 | B.V. | 77 | F | Diabetic nephropathy (Diabetes type 2) | 240 mg/dl compensated with 10 U. ready insulin | 230 mg/dl compensated with 10 U. ready insulin | 22.4 | 35.6 |

TABLE 3-continued

| | | | | Glycemia under fasting | | GFR Glomerulal Filtration Rate (Creatinine Clearance) | |
|---|---|---|---|---|---|---|---|
| abbr | Age | Gender | Diagnosis | T 0 | T 60 | T 0 | T 60 |
| Paz-06 | N.C. | 69 | F | Diabetic nephropathy (Diabetes 2) | 280 mg/dl compensated with 10 U. ready insulin + 20 U. retard insulin | 210 mg/dl compensated with 10 U. ready insulin + 20 U. retard insulin | 21.8 | 39.8 |

The results indicated above clearly show that PEA, in particular when administered orally in micronized or ultramicronized form, may be successfully used in the treatment of renal diseases in a mammal. Also diethanolamide of fumaric acid revealed to be active through intra-peritoneal injection.

The compounds of the invention may thus be used, both for humans and veterinary purposes, in the treatment of renal diseases.

Such diseases are preferably selected from among:
Diabetic nephropathy
Nephroangiosclerosis
Pyelonephrite
Polycystic kidney disease (polycystic kidney)
Alport syndrome
Lesch-Nyham syndrome
Goodpasture's syndrome
Lupus nephritis
Immunoglobulin A nephropathy
Tubular necrosis
Glomerulonephritis
Urethral stenosis
Iatrogenous nephropathies (from NSAIDs, from cytotoxic drugs, from Lithium, from antibiotics, from Cyclosporine, etc)
Nephropathies from therapeutic radiations
Nephropathies of the aged.

The compounds of the invention may thus be formulated for oral, buccal, parenteral, rectal or transdermal administration.

PEA may be preferably formulated for oral administration.

Diethanolamide of fumaric acid may be preferably formulated for oral or injection administration considering the high solubility of such synthetic molecule in water.

For oral administration, the pharmaceutical compositions may be provided, for example, in form of tablets or capsules prepared conventionally with pharmaceutically acceptable excipients such as binding agents (for example pregelatinised maize starch, polyvinylpyrrolidone or hydroxypropyl methylcellulose); bulking agents (such as for example lactose, microcrystalline cellulose or calcium hydrogen phosphate); lubricants (for example magnesium stearate, talc or silica); disintegrants (for example potato starch or sodium starch glycolate); or inhibitor agents (for example lauryl sodium sulfate). The tablets may be coated by means well known in the art. The liquid preparations for oral administration may be, for example, in form of solutions, syrups or suspensions or they may be in form of lyophilised products to be reconstituted, prior to use, with water or other suitable carriers. Such liquid preparations may be prepared through conventional methods with pharmaceutically acceptable additives such as suspension agents (for example sorbitol syrup, cellulose derivatives or edible hydrogenated fats); emulsifying agents (for example lecithin or acacia); non-aqueous carriers (for example almond oil, oily esters, ethylic alcohol or fractionated vegetable oils); and preservatives (for example methyl- or propyl-p-hydroxybenzoates or sorbic acid). The preparation may also suitably contain aromas, colouring agents and sweeteners.

The preparations for oral administration may be formulated suitably to allow the controlled release of the active ingredient.

For buccal administration, the compositions may be in form of tablets formulated conventionally, suitable for absorption at the buccal mucosa level. Typical buccal formulations are tablets for sublingual administration.

The compounds of the invention may be formulated for parenteral administration by injection. The formulations for the injection may be in form of one dose for example in a vial, with an added preservative. The compositions may be in such form as suspensions, solutions or emulsions in oily or aqueous carriers and they may contain formulary agents such as suspension, stabilising and/or dispersion agents. Alternatively, the active ingredient may be in form of powder to be reconstituted, prior to use, with a suitable carrier, for example with sterile water.

Diethanolamide of fumaric acid may be easily formulated in sterile and non-pyrogenic aqueous solutions according to conventional literature of the pharmaceutical industry.

According to the present invention, the compounds of the invention may also be formulated according to rectal compositions such as suppositories or retention enema, for example containing the basic components of common suppositories such as cocoa butter or other glycerides.

In addition to the compositions described previously, the compounds of the invention may also be formulated as deposit preparations. Such long-term formulations may be administered by implantation (for example subcutaneous, transcutaneous or intramuscular) or by intramuscular injection. Thus, for example, the compounds of the invention may be formulated with appropriate polymer or hydrophobic materials (for example in form of an emulsion in a suitable oil) or ionic exchange resins.

According to the present invention the dosage of a compound of the invention, or of mixtures thereof, proposed for administration to a man (with a body weight of about 70 Kg) ranges from 1 mg to 2 g and, preferably from 100 mg to 1 g of the active ingredient per dose unit. The dose unit may be administered, for example, from 1 to 4 times per day. The dosage shall be determined by the selected method of administration. It should be considered that frequent variations of the dose might be required depending on the age and the weight of the patient and also on the seriousness of the clinical condition to be treated. Lastly, the exact dose and method of administration shall be at the discretion of the doctor or veterinarian in question.

The pharmaceutical compositions of the invention may be prepared using conventional methods, such as those described in Remington's Pharmaceutical Sciences Handbook, Mack Pub. Co., N.Y., USA, 17th edition, 1985.

Following are non-exhaustive examples of pharmaceutical compositions according to the invention.

EXAMPLES OF FORMULATIONS

Example 1

Each tablet contains:

| | |
|---|---|
| PEAm | mg 300.00 |
| Microcrystalline cellulose | mg 78.47 |
| Sodium croscarmellose | mg 45.00 |
| Polyvinylpyrrolidone | mg 10.00 |
| Stearate magnesium | mg 4.00 |
| Polysorbate 80 | mg 2.00 |

Example 2

Each tablet contains:

| | |
|---|---|
| PEAum | mg 300.00 |
| Microcrystalline cellulose | mg 78.47 |
| Sodium croscarmellose | mg 45.00 |
| Polyvinylpyrrolidone | mg 10.00 |
| Stearate magnesium | mg 4.00 |
| Polysorbate 80 | mg 2.00 |

Example 3

Each tablet contains:

| | |
|---|---|
| PEAum | mg 600.00 |
| Microcrystalline cellulose | mg 156.94 |
| Sodium croscarmellose | mg 90.00 |
| Polyvinylpyrrolidone | mg 20.00 |
| Stearate magnesium | mg 8.00 |
| Polysorbate 80 | mg 4.00 |

Example 4

Each tablet contains:

| | |
|---|---|
| Diethanolamide of fumaric acid | mg 400.00 |
| Microcrystalline cellulose | mg 100.00 |
| Sodium croscarmellose | mg 80.00 |
| Polyvinylpyrrolidone | mg 15.00 |
| Stearate magnesium | mg 7.00 |
| Polysorbate 80 | mg 6.00 |

Example 5

A 5 g dose of oral-dissolvable microgranules, for paediatric use, contains:

| | |
|---|---|
| PEAum | mg 50.00 |
| Non-cariogenic sugar | mg 200.00 |
| Pharmaceutically acceptable excipients | q.s. to g 5.00 |

Example 6

A 5 ml dose of sterile suspension, for paediatric use, contains:

| | |
|---|---|
| PEAum | mg 80.00 |
| Carboxymethyl cellulose | mg 25.00 |
| Bi-distilled water | q.s. to ml 5.00 |

Example 7

A 5 g dose of oral-dissolvable microgranules, contains:

| | |
|---|---|
| PEAum | mg 600.00 |
| Non-cariogenic sugar | mg 200.00 |
| Pharmaceutically acceptable excipients | q.s. to g 5.00 |

Example 8

Each sterile single dose 5 ml two-layer container, contains:

In the aqueous gel:

| | |
|---|---|
| Hyaluronic acid sodium salt | mg 80.00 |
| Bi-distilled water | q.s. to ml 2.50 |

In the oily gel:

| | |
|---|---|
| PEAum | mg 600.00 |
| Monostearate glyceryl (Geleol) | mg 40.00 |
| vegetable oil | q.s. to ml 2.50 |

Example 9

Each soft gelatin capsule, for veterinarian use (dog and cat), contains:

| | |
|---|---|
| PEAum | mg 100.00 |
| Pharmaceutically acceptable oily excipients | mg 300.00 |

Example 10

A 2 ml glass vial contains:

| | |
|---|---|
| Diethanolamide of fumaric acid | mg 100.00 |
| Sterile saline solution | q.s. to ml 2.0 |

Example 11

A 4 ml lyophylised glass vial contains:

| | |
|---|---|
| Diethanolamide of fumaric acid | mg 200.00 |
| Glycocol | mg 85.00 |

A 4 ml solvent vial contains:

| | |
|---|---|
| Sterile saline solution | ml 4.0 ml |

What we claim is:

1. A method of treating a renal disease, consisting essentially of administering a therapeutically effective amount of diethanolamide of fumaric acid to a patient in need thereof, wherein said renal disease comprises chronic renal failure.

2. A method of treating a renal disease, consisting of administering a therapeutically effective amount of palmitoylethanolamide or of diethanolamide of fumaric acid and pharmaceutically acceptable excipients to a patient in need thereof, wherein said renal disease comprises chronic renal failure, and wherein said renal disease is selected from the group consisting of:
Diabetic nephropathy
Nephroangiosclerosis
Polycystic renal disease (polycystic kidney)
Immunoglobulin A nephropathy
Tubular necrosis
Urethral stenosis
Iatrogenous nephropathies (from NSAIDs, from cytotoxic drugs, from Lithium, from antibiotics, from Cyclosporine)
Nephropathies from therapeutic radiations
Nephropathies of the aged.

3. The method according to claim 1, wherein said renal disease is selected from the group consisting of:
Diabetic nephropathy
Nephroangiosclerosis
Polycystic renal disease (polycystic kidney)
Immunoglobulin A nephropathy
Tubular necrosis
Glomerulonephritis
Urethral stenosis
Iatrogenous nephropathies (from NSAIDs, from cytotoxic drugs, from Lithium, from antibiotics, from Cyclosporine)
Nephropathies from therapeutic radiations
Nephropathies of the aged.

* * * * *